April 12, 1938. H. B. BROOKINS Plant Pat. 272
ROSE
Filed April 22, 1936
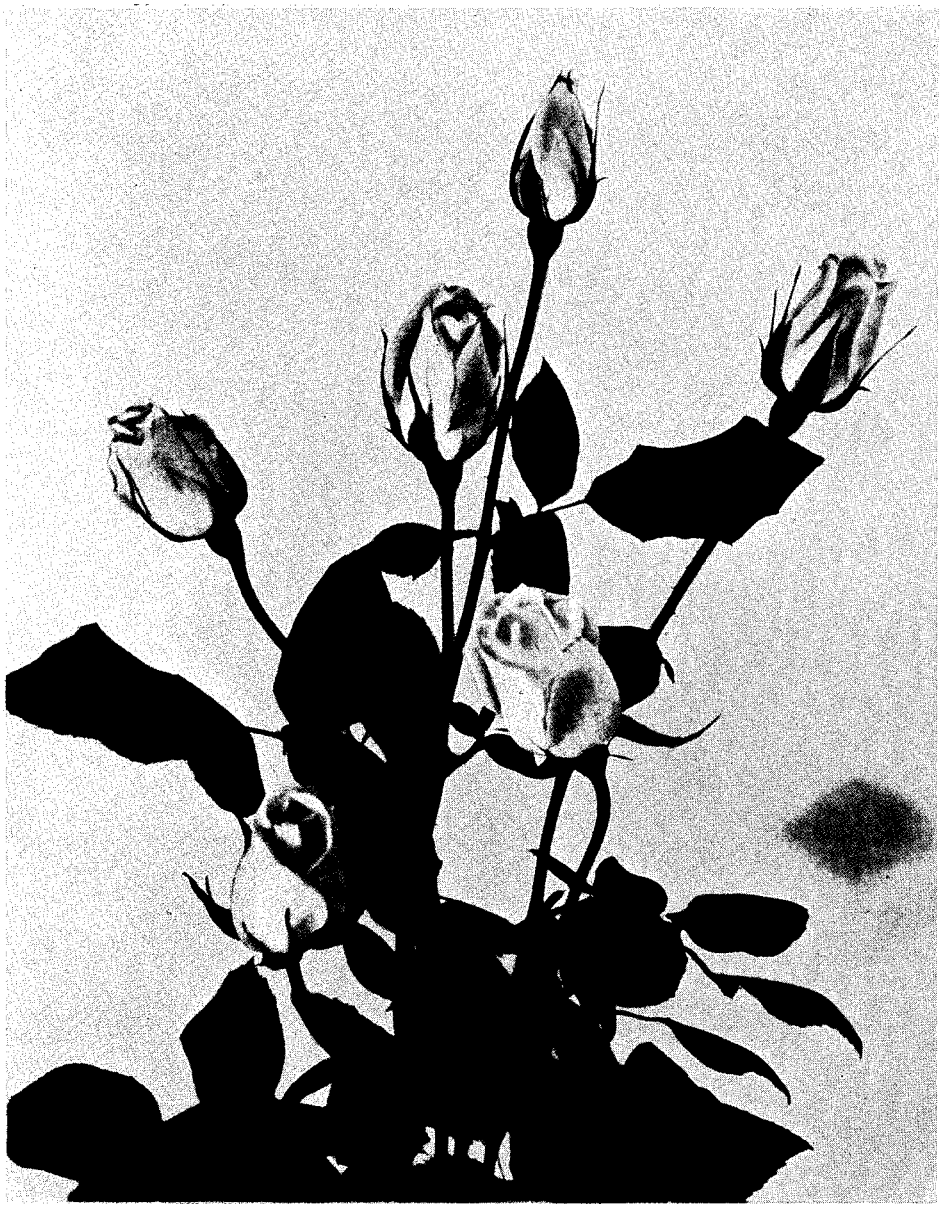
INVENTOR
Harold B. Brookins,
Beau, Brooks, Buckley & Beau.
ATTORNEYS Patented Apr. 12, 1938

Plant Pat. 272

UNITED STATES PATENT OFFICE

272

ROSE

Harold B. Brookins, Orchard Park, N. Y., assignor to Jerry Brookins, Inc., Orchard Park, N. Y.

Application April 22, 1936, Serial No. 75,899

1 Claim. (Cl. 47—61)

This discovery relates to a new and distinct variety of hybrid tea rose originated as a bud sport from the rose known as "Joanna Hill".

This new variety of rose possesses some of the characteristics of its parent, speaking particularly with reference to its prolific upright growth, dark green leathery foliage, relatively few thorns, and profuse production of flowers borne singly on long stems; thus making it particularly useful for cut flower purposes and ideally adaptable as a forcing rose. It possesses several characteristics making it distinctive from its parent, including color and shape of its bud and bloom. In coloring, it belongs generally in the range of the glowing tones of rich sun-ripened apricot, somewhat similar to the rose disclosed in U. S. Plant Patent No. 95, but distinctly different in many respects.

With reference to the colored plates opposite pages 256, 258 and 262 in "The Rose Manual" by J. H. Nicholas (Doubleday, Doran and Company, 1930), the unopened bud of this new rose may be described as darker than China pink. The bud is distinctive in shape, being a long yet firmly curving cone. As the bud begins to open, its outer petals assume a lemon coloring at the base and the body of the petals assumes a coloring between coral and salmon.

In the half open flower the color of the base of the petals ranges between straw and gold. The body of the petals is coral to salmon and the tips of the outer petals are touched with white tinted flesh. The center petals range in coloring between nankin and apricot.

In the three-quarter open bloom the base of the outside petals is saffron, the body of the petals coral, the tips of the outer petals touched with white tinted flesh, and the center petals range between chamois and copper.

In the full open flower the base of the petals is saffron, the outside body aurora, the tips of the outer petals touched with white tinted flesh, and the center petals range in coloring between nasturtium and aurora.

In the report of the U. S. Department of Agriculture, Bureau of Plant Industry, dated December 23, 1936, applicant's plant is described as follows, (based on the color standard used by applicant):

| *Tight bud* | *Color* |
|---|---|
| Base petals | Canary |
| Body petals | Hydrangea |
| *Half open* | |
| Base petal | Light canary |
| Body | Soft pink |
| *Full open* | |
| Base petal | Light canary |
| Body petal | Light soft pink |

The development of the bud into the bloom and the accompanying change in color is characterized by complete absence of magenta or purple tones, thereby making the variety very desirable as a forcing rose. The bud, being long pointed and tight and firm possesses great endurance and ability to withstand abuse and changes in temperature and moisture conditions, thus making it an unusually good shipper. This new variety has proven itself to be a prolific greenhouse winter blooming variety. In addition, this new variety is an improvement over its parent in that the bud has the ability to remain in its partly developed condition for a longer period.

A detail description of this new variety of rose plant is as follows:

Parentage:
Sport of variety "Joanna Hill".

Classification:
Botanic and commercial—hybrid tea.

*Flower*

Blooming habit:
Blooms profusely.

Recurrent:
Continuous, even during winter months, produces a large flower which does not turn purple when old.

Other habits:
Disease resistant; prolific grower and bloomer; an excellent shipper. Flowers are double on very long stems from natural cut.

Bud:
*Size.*—Medium.
*Form.*—Long and pointed.
*Sepals.*—Serrated, hood above bud; often remain embracing bloom when open.
*Calyx.*—Pear shape. Large size. Aspect—outer smooth and inner hairy.
*Peduncle.*—Medium length. Aspect slightly hirsute. Color medium green. Strength medium.

Bloom:
*Size.*—Large; average size when fully opened about four inches or larger.
*Borne.*—Singly.
*Stems.*—Long.
*Form.*—When first open high center. Permanence—retains its form to the end; flattens and cups slightly.
*Petalage.*—Double (many petals and stamens hidden). Number of petals under normal conditions around 30.
*Variegations.*—Slightly veined in deeper color.
*Discoloration.*—General tonality lightens and becomes delicately tinged with shell-pink.

Petals:
*Texture.*—Thick; unaffected by adverse weather conditions.
*Appearance.*—Inside and outside dully satiny.
*Form.*—Obovate.
*Arrangement.*—Imbricated (shingle like), few small petaloids in center.
*Persistence.*—Hang on and dry.
*Fragrance.*—Moderately fragrant.
*Lasting quality.*—Very long while on the plant or after being cut.

Genital Organs:
*Stamens, anthers.*—Medium, many. Color—deep yellow—mixed with petaloids.
*Stamens, filaments (threads) medium.*—Color—yellow.
*Pollen.*—Light orange.
*Styles.*—Bunched, long.
*Stigmas.*—Color, red.
*Ovaries.*—Some protruding from calyx.

*Plant*

Form:
Bush.

Growth:
Very prolific.

Foliage:
Leaflets mostly five—few seven.
*Size.*—Very large.
*Quantity.*—Abundant.
*Color.*—New foliage, bronzy-red through light green shaded with bronze to deep green in the mature foliage.
*Shape.*—Oval, acute tip, blunt base.
*Texture.*—Upper side leathery, glossy, smooth; under side slightly velvety; ribs and veins ordinary.
*Edge.*—Serrated.
*Serration.*—Single, small, sharp.
*Leaf stem.*—Under side smooth and light green color; slightly reddish on top.
*Stipules.*—Medium, finely serrated.
*Disease resistance.*—Resistant.

Wood:
*New wood.*—Color bronzy green; bark smooth.
*Old wood.*—Color green to brown; bark smooth.
*Thorns.*—Quantity—medium. Form, medium size flat base; hooked downward. Color when young, red. Position—irregular.
*Prickles.*—None.
*Short needles.*—On main stalks few to none. On laterals none.

I claim:

A new and distinct variety of hybrid tea rose plant, characterized by its prolific growth and winter-blooming habit, accompanied by the free production on long stems of blooms of novel form, substance and color, substantially as shown and described.

HAROLD B. BROOKINS.